United States Patent
Tsai

(10) Patent No.: US 11,478,534 B1
(45) Date of Patent: Oct. 25, 2022

(54) FORMULATION AND METHOD OF PREPARING ZINC-CHARGED INSULIN FOR ORAL ADMINISTRATION

(71) Applicant: America Great Health, Alhambra, CA (US)

(72) Inventor: Men Hwei Tsai, Alhambra, CA (US)

(*) Notice: Subject to any disclaimer, the term of this patent is extended or adjusted under 35 U.S.C. 154(b) by 0 days.

(21) Appl. No.: 17/374,317

(22) Filed: Jul. 13, 2021

(51) Int. Cl.
*A61K 38/28* (2006.01)
*A61P 3/10* (2006.01)
*A61K 9/00* (2006.01)
*A61K 47/52* (2017.01)

(52) U.S. Cl.
CPC ............ *A61K 38/28* (2013.01); *A61K 9/0053* (2013.01); *A61K 47/52* (2017.08); *A61P 3/10* (2018.01)

(58) Field of Classification Search
CPC ............ A61K 38/28; A61K 47/52; A61P 3/10
See application file for complete search history.

(56) References Cited

U.S. PATENT DOCUMENTS

2010/0120660 A1* 5/2010 Balschmidt ............... A61P 3/10
514/1.1

OTHER PUBLICATIONS

Nabarro and Stowers, British Med. Journal, pp. 1027-1030, Nov. (1953).*
Maares M, Haase H, A Guide to Human Zinc Absorption: General Overview and Recent Advances of In Vitro Intestinal Models, Nutrients, 2020;12(3):762. Published Mar. 13, 2020. doi: 10.3390/nu12030762.
Petukh, M. et al., Predicting Nonspecific Ion Binding Using DelPhi, Biophysical Journal, Jun. 2012, vol. 102, 2885-2893, Published 2012 by Biophysical Society, doi: 10.1016/j.bpj.2012.05.013.

* cited by examiner

*Primary Examiner* — Gyan Chandra
(74) *Attorney, Agent, or Firm* — Trojan Law Offices

(57) ABSTRACT

This invention is directed to a zinc-charged insulin composition that is effective in treating diabetes and lowering and stabilizing blood glucose levels when administered orally. The zinc-charged insulin is acid and enzyme resistant, such that the zinc-charged insulin is capable of surviving the acidic conditions of the stomach. The zinc-charged insulin is capable of being absorbed through the gastrointestinal tract and stored in the liver, such that the zinc-charged insulin is long lasting and pharmacokinetically similar to the insulin normally generated by the body. The invention is further directed to a method of preparing the zinc-charged insulin composition, including: (1) removing any loosely bound surface ions present on an insulin molecule using a chelating agent; and (2) replacing all the loosely bound surface ions with zinc.

4 Claims, 14 Drawing Sheets

FORMULATION AND METHOD OF PREPARING ZINC-CHARGED INSULIN FOR ORAL ADMINISTRATION

FIELD OF THE INVENTION

The present invention relates generally to a formulation for zinc-charged insulin that is available to be administered orally, as well as a method of turning insulin into a form that is available for oral administration.

BACKGROUND OF THE INVENTION

One of the most well-known macromolecules produced by the body is the hormone insulin. Generally, insulin is a protein hormone produced by the pancreas and used by the liver, fat, and muscles to regulate the concentration of blood glucose. The secretion of insulin regulates the concentration of glucose in the blood, such that the level of blood glucose is always stable, whether the body is undergoing fasting or feeding.

Diabetes Mellitus ("diabetes") is a disease in which the pancreas does not release insulin in sufficient levels to regulate blood glucose (Type 1 diabetes) or in which the body builds up a resistance to insulin (Type 2 diabetes). According to the United States Centers for Disease Control and Prevention ("CDC"), diabetes affects approximately 34 million Americans, or a little over 1 in 10 Americans. Additionally, approximately 1 in 3 Americans are prediabetic, where their blood glucose levels are higher than average but not to diabetic levels yet. According to the CDC, diabetes was the seventh leading cause of death in the United States in 2017. Thus, diabetes is a significant health issue prevalent in the United States, among many other nations.

Generally, diabetes can result from either the pancreas failing to produce insulin in sufficient levels, and/or the body building up a resistance to insulin such that muscle, fat, and liver cells respond poorly to normal levels of insulin. Type 1 diabetes is the result of the pancreas failing to produce insulin. Thus, patients with type 1 diabetes must administer insulin to themselves to make up for the missing hormone. Type 2 diabetes is generally caused by either insulin resistance or a combination of insulin resistance and insufficient release of insulin from the pancreas. Type 2 diabetes similarly requires a patient to self-administer insulin to themselves as well. Type 2 diabetes is the most common form of diabetes in the United States, accounting for 90%-95% of all diabetes cases in the United States.

There are currently numerous tests for determining whether a patient has diabetes. For example, a patient may be given a glucose tolerance test, an insulin resistance test, or a test to determine how much Glycated Hemoglobin, or Hemoglobin $A_{1c}$ ($HbA_{1c}$), to determine the average level of blood glucose over time. For $HbA_{1c}$ tests, the higher the level of $HbA_{1c}$, the higher the level of blood glucose, indicating the presence of diabetes. Furthermore, generally testing the level of glucose in the blood after the administration of insulin can indicate whether the patient has absorbed the insulin, as the blood glucose levels of diabetic patients should drop to stable levels after administration of insulin.

The current method for administering insulin to a patient is through subcutaneous injection, where the insulin is injected into the tissue between the skin and muscle with a small needle. This injection is generally done in the abdomen of a patient to enable an effective amount of the insulin to be absorbed by the body. This is currently the most common and preferred method of effectively administering insulin to a patient.

However, subcutaneous injections to administer insulin have some drawbacks. For example, subcutaneous injection of insulin presents the possibility of complications, such as infection of the injection site, and typically require a patient to rotate injection sites, which can cause pain and discomfort.

Another important drawback is insulin administered through subcutaneous injection does not reflect the natural physiological and pharmacokinetic conditions of insulin inside the body. Typically, nearly all of the insulin secreted from the pancreas is stored in the liver. However, when insulin is administered through subcutaneous injection, it typically gets stored in muscle and fat tissues instead of the liver. Thus, the insulin administered through subcutaneous injection is not as pharmacokinetically similar to the insulin produced by the body.

However, insulin administered orally would likely ultimately end up in the liver. Food will generally be absorbed by the liver through the portal vein, as with most food ingested by a subject. Thus, it is expected that insulin orally administered would end up in the liver through the same process, resulting in an insulin medicine that is pharmacokinetically very similar to natural insulin produced by the body. As such, an insulin capable of being administered orally is a more ideal medicine than an insulin only administered through subcutaneous injection.

However, insulin, as with other macromolecules, were not as effective in treating diabetes unless administered through subcutaneous injection. Insulin, as with other macromolecules, are typically destroyed in the stomach by the stomach acid and enzymes, such that the hormone cannot make it to the GI tract to be sufficiently absorbed by the body.

Due to the inability of insulin to generally survive the acidic conditions of the stomach, it is very challenging to administer insulin orally. However, administration of insulin orally is preferred over subcutaneous injection due to the less intrusive nature of oral administration versus injections and the natural physiological and pharmacological effects of the oral insulin on the body. As of the filing of this application, Applicant is not aware of any oral insulin product that is approved by the FDA. However, should a technique be developed such that insulin may be administered orally, the industry could rapidly become a multi-billion dollar industry.

As such, there is a need for an insulin composition that may be administered orally and still effectively be absorbed by the body. Additionally, there is a need for a technique to make insulin that is capable of being orally administered and effectively absorbed by the body. Additionally, there is a need for a technique to convert other subcutaneous injection insulin products on the market, such as insulin Glargine and insulin Lispro into insulin that may be effectively administered orally.

SUMMARY OF THE INVENTION

The invention disclosed herein is generally a zinc-charged insulin composition that may be effectively administered orally. Further, a method of preparing the zinc-charged insulin composition is disclosed. The method of preparing the zinc-charged insulin composition generally includes the following steps: (1) removing any loosely bound surface ions present on a general insulin molecule using a chelating agent; and (2) replacing all the loosely bound surface ions with Zinc.

It is an object of the present invention to provide an insulin composition that may be administered orally and still effectively be absorbed by the body. As such, it is an object of the present invention to provide an insulin composition capable of surviving the acidic nature of the stomach and reaching the gastrointestinal ("GI") tract, and effectively be absorbed by the GI tract into the bloodstream.

It is another object of the present invention to create a method to make insulin that is capable of being orally administered and effectively absorbed by the body.

It is yet another object of the present invention to create a method for converting other subcutaneous injection insulin products on the market, such as insulin Glargine and insulin Lispro, into insulin that may be effectively administered orally.

BRIEF DESCRIPTION OF THE DRAWINGS

These and other features and advantages of the present invention will become appreciated, as the same becomes better understood with reference to the specification, claims and drawings herein:

DETAILED DESCRIPTION OF THE INVENTION

Figure 1:
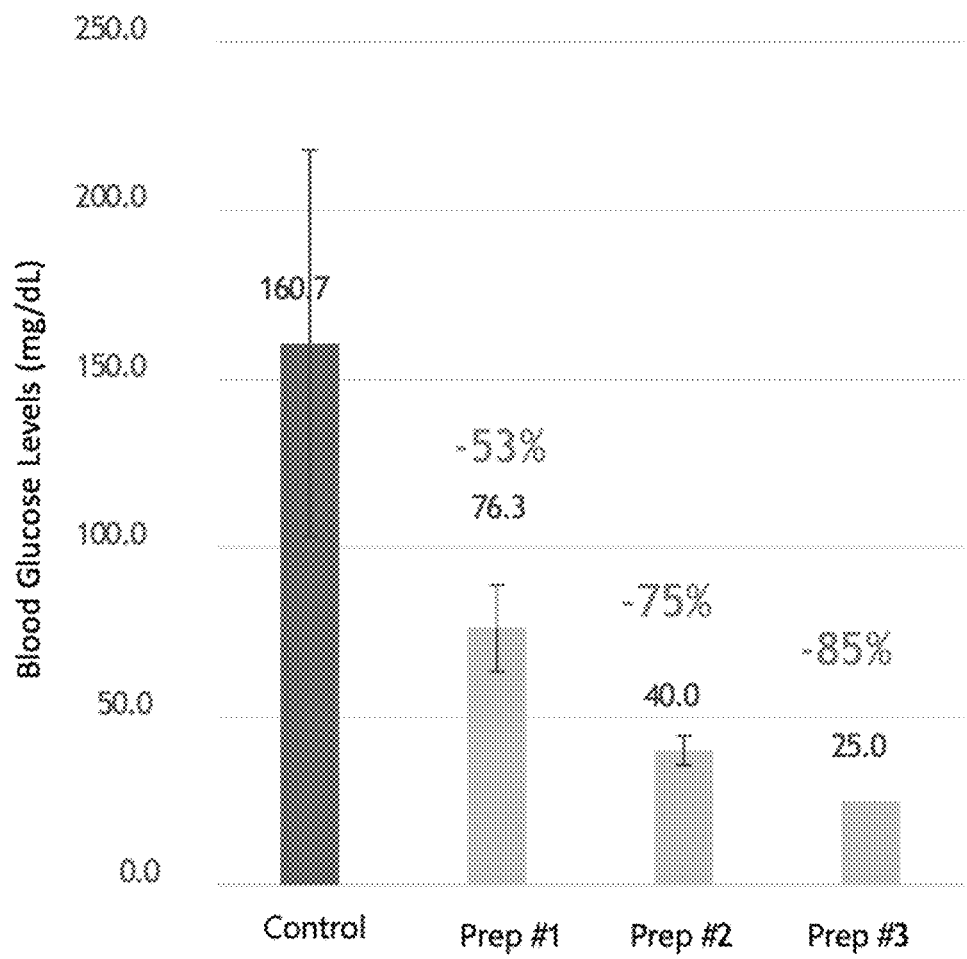
FIG. 1 is a graph of the blood glucose levels of mice who ingested the zinc-charged insulin in three doses as compared to a control.

The invention now will be described more fully hereinafter with reference to the accompanying drawings, in which embodiments of the invention are shown. This invention may, however, be embodied in many different forms and should not be construed as limited to the embodiments set forth herein. Rather, these embodiments are provided so that this disclosure will be thorough and complete, and will fully convey the scope of the invention to those skilled in the art.

It will be understood that when an element is referred to as being "on" another element, it can be directly on the other element or intervening elements may be present there between. As used herein, the term "and/or" includes any and all combinations of one or more of the associated listed items.

It will be understood that, although the terms first, second, third etc. may be used herein to describe various elements, components, regions, layers and/or sections, these elements, components, regions, layers and/or sections should not be limited by these terms. These terms are only used to distinguish one element, component, region, layer or section from another element, component, region, layer or section.

As used herein, the singular forms "a," "an," and "the," are intended to include the plural forms as well, unless the context clearly indicates otherwise. It will be further understood that the terms "comprises" and/or "comprising," "includes" and/or "including," and "have" and/or "having," when used in this specification, specify the presence of stated features, regions, integers, steps, operations, elements, and/or components, but do not preclude the presence or addition of one or more other features, regions, integers, steps, operations, elements, components, and/or groups thereof.

Furthermore, relative terms, such as "lower" or "bottom," and "upper" or "top," and "inner" or "outer," may be used herein to describe one element's relationship to another elements as illustrated in the Figures. It will be understood that relative terms are intended to encompass different orientations of the device in addition to the orientation depicted in the Figures.

Unless otherwise defined, all terms used herein have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and the present disclosure, and will not be interpreted in an idealized or overly formal sense unless expressly so defined herein.

Exemplary embodiments of the present invention are described herein with reference to idealized embodiments of the present invention. As such, variations from the shapes of the illustrations as a result, for example, of manufacturing techniques and/or tolerances, are to be expected. Thus, embodiments of the present invention should not be construed as limited to the particular shapes of regions illustrated herein but are to include deviations in shapes that result, for example, from manufacturing.

This patent application describes a zinc-charged insulin composition and a method of making thereof. Unlike uncharged insulin molecules that have not been charged with zinc, the zinc-charged insulin composition may be effectively administered orally. "Uncharged insulin" from here on refers to insulin macromolecules and insulin products that have not yet been charged with zinc. Generally, the zinc-charged insulin composition includes a "zinc ion cloud" on the surface of the insulin molecule. This zinc ion cloud allows the insulin molecules to survive the acidic conditions of the stomach and permits the insulin to be effectively absorbed by the GI tract.

A method of preparing the zinc-charged insulin composition is also disclosed. The method of preparing the zinc-charged insulin composition includes the following steps: (1) removing any loosely bound surface ions present on a general insulin molecule using a chelating agent; and (2) replacing all the loosely bound surface ions with zinc using a zinc compound. Importantly, this method may be used on subcutaneous injected insulin products currently on the market, such as insulin Lispro and insulin Glargine, to convert the injected insulin into insulin that is capable of being effectively administered orally.

(1) The Zinc-Charged Insulin Composition

Disclosed herein is a zinc-charged insulin composition that may be effectively administered orally. The zinc-charged insulin composition has an insulin molecule having zinc ions loosely bound to the insulin molecule. These zinc ions loosely bound to the surface of the insulin molecule form the "zinc ion cloud" on the insulin molecule's surface. The presence of this zinc ion cloud permits the insulin molecules to survive the acidic conditions of the stomach and permits the insulin to be effectively absorbed by the GI tract.

Preferably, a molar ratio of insulin to zinc is 1:136. While other molar ratios may be utilized without departing from the concepts disclosed herein, this particular ratio is preferred for replacing all of the insulin surface ions with zinc. The preparation of this composition is discussed in the method section found below.

Once the zinc-charged insulin is prepared, the zinc-charged insulin composition may be administered in any form suitable for oral ingestion. For example, the zinc-charged insulin may be administered as a capsule containing the zinc-charged insulin, a pressed tablet of the zinc-charged insulin, a liquid form of the zinc-charged insulin, or any other means for oral administration known in the art. The important aspect to this composition is the fact that the zinc-charged insulin may be effectively administered orally, regardless of the means of oral administration. Thus, any means of oral administration may be utilized without departing from the concepts disclosed herein.

Once the zinc-charged insulin is administered to a subject orally, the insulin macromolecules will pass through the esophagus and enter the stomach. Generally, uncharged insulin is unable to survive the acidic stomach conditions and is dissolved and/or destroyed by the hydrochloric acid and digestion enzymes present in the stomach. However, zinc is known to degrade hydrochloric acid by the following chemical reaction: $Zn + 2HCl \rightarrow ZnCl_2 + H_2$. Thus, the presence of the zinc ion cloud on the insulin molecule results in the zinc-charged insulin being acid resistant, as the hydrochloric acid is neutralized by the zinc ion cloud instead of reacting with the insulin macromolecule, thereby protecting the insulin macromolecule from digestion. Further, the hydrochloric acid and acidic conditions of the stomach are required for the peptic enzymes in the stomach to digest proteins. Thus, the zinc ions neutralizing the hydrochloric acid in the stomach further prevent the peptic enzymes from effectively digesting the insulin molecules. Thus, the zinc-charged insulin is also resistant to the digestive enzymes in the stomach as well as the hydrochloric acid. This novel approach permits the zinc-charged insulin to survive and pass through the stomach and enter the GI tract to be absorbed into the blood stream.

Once the zinc-charged insulin enters the GI tract, it is able to be absorbed into the liver by the intestine villi. Due to the zinc ion cloud on the surface of the insulin macromolecule, a significant amount of the insulin is able to be absorbed by the intestine to be delivered to the liver and throughout the body.

One potential reason for the intestine absorbing a substantial amount of zinc-charged insulin has to do with how zinc is generally absorbed by the intestine. Generally, zinc is absorbed in the intestine through a "Zinc Transporter," which is a group of zinc-binding proteins in the intestine villi. The zinc ion cloud of the zinc-charged insulin may interact with these Zinc Transporters, thereby transporting the zinc-charged insulin from the intestine villi to the liver. Thus, these Zinc Transporters may help the zinc-charged insulin be absorbed by the intestine villi, thereby allowing a significant amount of insulin to be absorbed by the body and stored in the liver.

Importantly, the absorption of the zinc-charged insulin through intestine villi by these Zinc Transporters allows the zinc-charged insulin to be absorbed and stored by the liver. Thus, the zinc-charged insulin will be pharmacokinetically similar to the insulin generated by the body, as it is stored and slowly released by the liver instead of fat and muscle tissues as with subcutaneously injected insulin. Furthermore, having the zinc-charged insulin stored and slowly released by the liver allows for the slow, controlled release of insulin into the bloodstream. This allows the zinc-charged insulin to last significantly longer in the body than insulin administered through subcutaneous injection, thereby requiring less frequent administration to maintain stable blood glucose levels. These long-lasting effects were further confirmed by the examples as provided below.

In a preferred embodiment, a patient may be orally administered between 10 and 15 mg of the zinc-charged insulin. This amount of zinc-charged insulin may be administered pro re nata, and preferably at least once per week due to the long-lasting nature of the zinc-charged insulin. Based upon the preferred molar ratio of insulin to zinc, the total zinc administered to a patient in a single day will be between 53 and 88 mg. As such, the amount of zinc administered in a single day are within safe ranges for oral consumption by humans.

As described in the below examples, a significant amount of insulin was absorbed by the intestine. For example, after orally feeding the zinc-charged insulin to mice, it was determined that approximately 42% of the insulin was absorbed by the intestine. This effectivity was further confirmed by the effect of the zinc-charged insulin on blood glucose levels in human subjects, as well as the continued presence of insulin in the human subject's blood stream up to 14 day post-ingestion, as shown in the examples described below.

(2) The Method of Preparing the Zinc-Charged Insulin Composition

Generally, the method of preparing the zinc-charged insulin composition includes the following steps: (1) removing any loosely bound surface ions present on a general insulin molecule using a chelating agent; and (2) replacing all the loosely bound surface ions with zinc using a zinc compound. Each of these steps will be discussed in turn.

(A) Removal of Surface Ions from Insulin Molecule

The first step in this method involves taking an insulin molecule and removing all the surface ions from the insulin molecule. Before initiation of this method, the uncharged insulin molecule, as with other macromolecules, may contain numerous ions either directly bound to the insulin molecule or loosely bound to the insulin molecule. These ions may be specifically bound to the insulin molecule and associated with a specific function of the molecule or may be nonspecifically bound to the surface of the insulin molecule without a specific function or purpose. Some of these ions are loosely bound to the insulin molecule, presumably due to an electrostatic attraction between the insulin and ions that is sufficiently strong to immobilize the ions.

The first step in this method is to remove all of these surface ions from the uncharged insulin molecule using a chelating agent. The chelating agent pulls off and binds with the surface ions of the insulin molecule, such that the surface ions are removed from the insulin molecule. Once the chelating agent removes the surface ions from the insulin molecule, the insulin molecule will be ready for the second step in the method.

The preferred chelating agent for removing the surface ions off the insulin molecule is ethylenediaminetetraacetic acid ("EDTA"). However, other chelating agents, including but not limited to dimercaprol, dimercaptosuccinic acid ("DMSA"), and egtazic acid ("EGTA"), may be utilized as the chelating agent without departing from the concepts disclosed herein.

In one embodiment of the method, the uncharged insulin is incubated with EDTA in order to remove the surface ions from the uncharged insulin molecules. Generally, the uncharged insulin is incubated for at least one hour with EDTA to chelate the surface ions from the uncharged insulin. In a preferred embodiment, the uncharged insulin is incubated with EDTA for one hour. In other embodiments, the uncharged insulin may be incubated with EDTA for longer than one hour. The general concentrations of uncharged insulin and EDTA during this incubation are based on a ratio of 1:5 insulin to EDTA. This general concentration ratio is sufficient to chelate all of the surface ions from the uncharged insulin. In one preferred embodiment, the 1 mM of insulin is incubated with 5 mM EDTA for one hour. Once the incubation is complete, the uncharged insulin will have all the surface ions removed, such that the molecules are ready to be charged with Zinc.

In a preferred preparation embodiment, 56 mg of insulin is incubated with 12 mL of 10% acetic acid and 1.5 mL of 130 mM EDTA for one-to-two hours. The result of this incubation will be insulin that has had its surface ions stripped by the EDTA, such that the insulin molecule is ready to incubation with the zinc compound.

(B) Replacement of Surface Ions from Insulin Molecule with Zinc

The second step in this method involves replacing the removed surface ions of the uncharged insulin molecule with zinc. Once the incubation of insulin with the chelating agent is complete, the incubated insulin mixture is then incubated with a zinc compound. The incubation of the incubated insulin mixture with the zinc compound replaces all of the loosely bound surface ions with zinc ions. This treatment creates a "zinc ion cloud" on the insulin surface.

In the preferred embodiment, the zinc compound is zinc acetate. Other potential zinc compounds include but are not limited to zinc oxide, zinc sulfate, and zinc nitrate. Any zinc compound may be used so long as the compound is capable of producing zinc ions that will ultimately create the zinc ion cloud on the insulin surface.

In the preferred embodiment of the method, the incubated insulin mixture is incubated for at least three hours with zinc acetate. This second incubation replaces all of the surface ions that were removed from the uncharged insulin molecule with zinc ions. While it is preferred to incubate the incubated insulin mixture with zinc acetate for at least three hours, different incubation periods may be used as required, especially for different zinc compounds, without departing from the concepts disclosed herein. Once this second incubation is complete, the insulin will have been charged with the zinc ions, resulting in the zinc-charged insulin composition. The zinc-charged insulin molecules thus have a zinc ion cloud on the surface of the insulin molecules.

In the preferred preparation embodiment described above, the resulting mixture from the one-to-two hour incubation of 56 mg of insulin, 12 mL of 10% acetic acid, and 1.5 mL of EDTA (130 mM), is then incubated with 3 mL of zinc acetate (500 mM) for three hours. The result of this second incubation is the zinc-charged insulin compound. Based on the above preferred preparation, the final molar concentration of insulin is 0.58 mM, and the final molar concentration of zinc is 79 mM. Thus, in the preferred preparation of the zinc-charged insulin composition, the molar ratio of insulin to Zinc is 1:136.

While preferred ratios, concentrations, and compounds are discussed throughout the disclose of this method, other ratios, concentrations, and compounds may be utilized without departing from the general method disclosed herein.

(3) Conversion of Uncharged, Injected Insulin Products into Zinc-Charged Insulin This method not only allows for the preparation of a zinc-charged insulin capable of being administered orally and absorbed by the GI tract, but also can convert other uncharged insulin products designed for subcutaneous injection into zinc-charged insulin for oral administration. For example, the fast-acting, injected insulin manufactured by Eli Lilly & Co. called insulin Lispro may be converted into oral insulin through the general method disclosed. As with uncharged insulin, incubating the insulin Lispro with a chelating agent, such as EDTA, followed by a zinc compound, such as zinc acetate, results in a zinc-charged insulin Lispro compound. This zinc-charged insulin Lispro compound has the zinc ion cloud surrounding insulin Lispro molecules, such that the compound is capable of being administered orally as described above.

Figure 16:
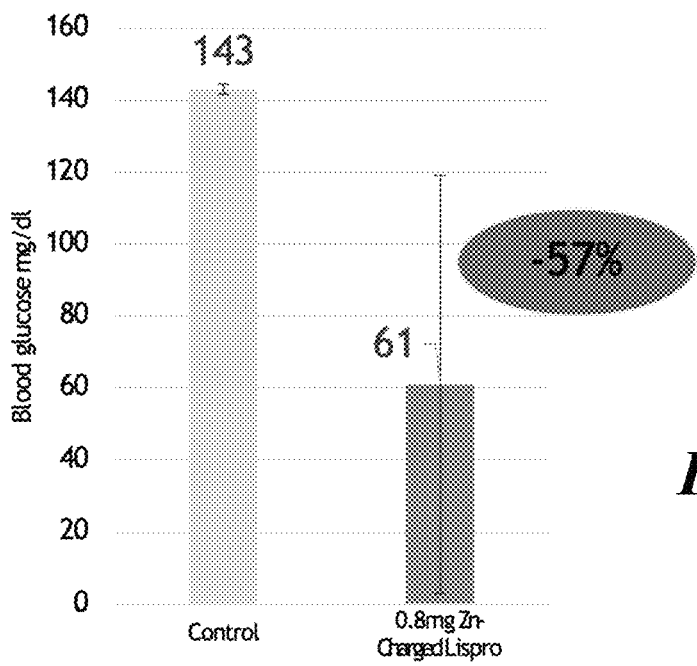
FIG. 16 is a graph depicting the efficacy of converting insulin Lispro into zinc-charged insulin for oral administration, as compared to a control.

To determine whether the method was effective in converting other uncharged insulin products into zinc-charged insulin, a preparation of zinc-charged insulin Lispro or a control of uncharged insulin Lispro were prepared via the above discussed method. Each of these preparations also contained 10 mg of glucose. Once the preparation was complete, the preparations were orally administered to mice. To determine the effectiveness of the zinc-charged insulin Lispro, mice were orally administered either 0.8 mg of zinc-charged insulin Lispro or the control, and their blood glucose levels were measured 2.5 hours later. The level of glucose in the blood of the mice who were given the control was approximately 143 mg/dL. However, the mice who were given the zinc-charged insulin Lispro had a blood glucose level of 61 mg/dL, or a 57% decrease, as depicted in FIG. 16. Thus, this method of preparing zinc-charged insulin Lispro for oral administration was effective in reducing and stabilizing the mice's blood glucose, just as if it was given through subcutaneous injection.

Additionally, the long-lasting insulin manufactured by Sanofi S.A., insulin Glargine, sold under the brand name "Lantus®", may be converted into zinc-charged insulin through the same method. This subcutaneously injected uncharged insulin product is considered the best-selling insulin drug on the market, as this uncharged insulin lasts up to 24 hours in the body and results in stable blood glucose levels for 24 hours. As with other forms of uncharged insulin, incubating the insulin Glargine with a chelating agent, such as EDTA, followed by a zinc compound, such as zinc acetate, results in a zinc-charged insulin Glargine compound that is capable of being orally administered.

Figure 17:
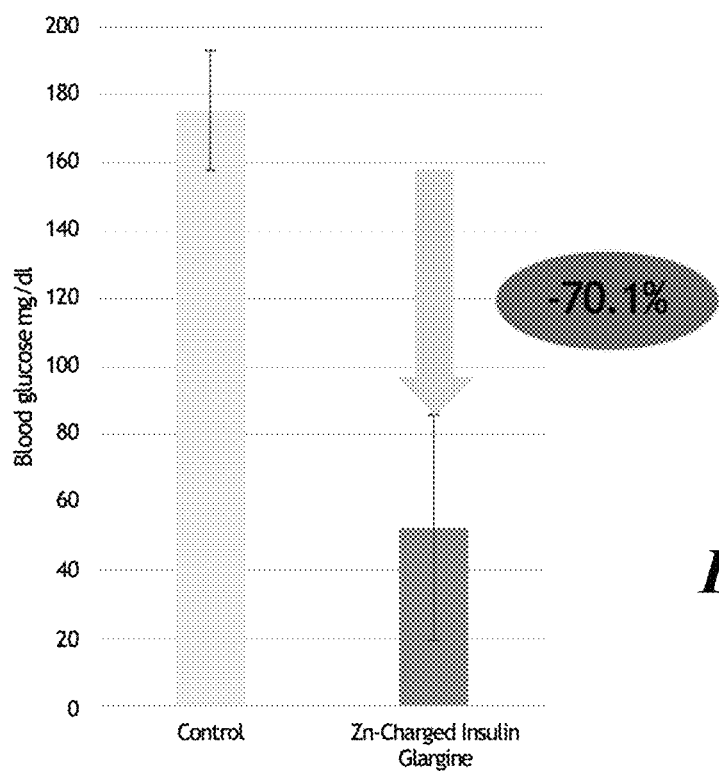
FIG. 17 is a graph depicting the efficacy of converting insulin Glargine into zinc-charged insulin for oral administration, as compared to a control.

As shown in FIG. 17, when mice were orally fed the zinc-charged insulin Glargine, the levels of blood glucose were reduced by 70%. To determine the effectiveness of the zinc-charged insulin Glargine, mice were orally administered preparations of either 250 μg of zinc-charged insulin Glargine or a control of uncharged insulin Glargine, each preparation also containing 10 mg of glucose, and their blood glucose levels were measured 3 hours later. In the mice who were orally given the control, the level of glucose in their blood was approximately 175 mg/dL. However, the mice who were orally given the zinc-charged insulin Glargine had a blood glucose level of approximately 50 mg/dL, or a 70.1% decrease. Thus, this method of preparing zinc-charged insulin Glargine for oral administration was effective in reducing and stabilizing the mice's blood glucose, just as if it was given through subcutaneous injection.

While the two above examples were performed on mice, it is expected that these same results will be achieved when administering these products to humans. The effectiveness of the oral administration of the general zinc-charged insulin compound was found to be effective on humans after the testing with mice described below. As such, it is expected that converting these other uncharged, injected insulin products into zinc-charged insulin compounds for oral administration using the disclosed method will not affect the effectiveness of these uncharged insulin compounds in regulating, reducing, and stabilizing blood glucose levels.

These are two examples of how the method and concepts disclosed may convert other uncharged, injectable insulin products on the market into zinc-charged insulin that may be orally administered effectively. It is expected that this method will similarly convert any other uncharged, subcutaneous injection insulin into zinc-charged insulin that is capable of being orally administered.

Examples (1) Zinc-Charged Insulin Orally Administered: Effects in Mice

Testing was first performed on mice to determine the efficacy of the zinc-charged insulin orally administered. FIGS. 1-6 provide the graphs depicting the results of the testing on mice.

FIG. 1 depicts the dose response of mice who given the zinc-charged insulin in varying doses. This test was performed to determine the efficacy of different doses on the mice subjects. Here, mice were orally given four different doses of insulin containing 10 mg of glucose. The first dose given to the mice was the control of uncharged insulin, while the other three doses contained varying doses of the zinc-charged insulin. The control dose of uncharged insulin orally administered in the amount of 2.5 mg per mouse. Dose #1 contained the zinc-charged insulin dosed at 0.25 mg per mouse. Dose #2 contained the zinc-charged insulin dosed at 0.3 mg per mouse. Dose #3 contained the zinc-charged insulin dosed at 1.3 mg per mouse. The blood glucose levels of the mice were then measured three hours post-ingestion of the four doses.

The levels of blood glucose in these mice are depicted in the graph shown in FIG. 1. As shown, the blood glucose level in the mice given the control preparation was 160.7 mg/dL. This high level of blood glucose indicates that the uncharged insulin of the control was not absorbed by the mice's body, thus resulting in a high blood glucose level. The blood glucose levels of the mice given the zinc-charged insulin were significantly lower. For the mice given Dose #1 (0.25 mg zinc-charged insulin per mouse), their blood glucose levels were measured at 76.3 mg/dL, or a 53% reduction from the control. For the mice given Dose #2 (0.3 mg zinc-charged insulin per mouse), their blood glucose levels were measured at 40.0 mg/dL, or a 75% reduction from the control. Lastly, for the mice given Dose #3 (1.3 mg zinc-charged insulin per mouse), their blood glucose levels were measured at 25.0 mg/dL, or an 85% reduction from the control.

This graph highlights the efficacy of this zinc-charged insulin orally administered. Oral administration of uncharged insulin is generally ineffective, as the stomach acid and digestion enzymes dissolve and destroy the macromolecule before it is able to be absorbed. As discussed above, this is highlighted by the mice orally given the control, or uncharged insulin. These mice did not see any drop in their blood glucose levels 3 hours after oral administration of the uncharged insulin. However, each of the mice orally administered the varying doses of the zinc-charged insulin had significant reductions in their blood glucose levels when compared to the control, highlighting the ability for the zinc-charged insulin to survive the stomach conditions and be absorbed into the body. Thus, these dose tests on mice highlight the efficacy of this zinc-charged insulin when orally administered.

Figure 2:
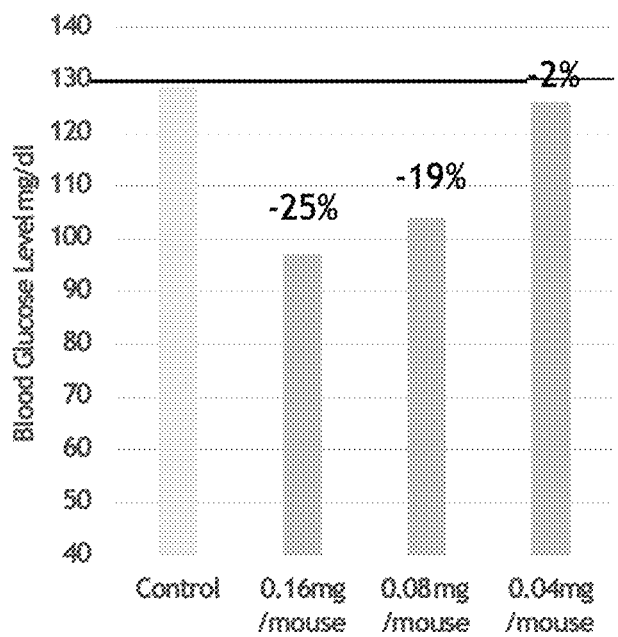
FIG. 2 is a graph of the blood glucose levels of mice who ingested the zinc-charged insulin in three low doses as compared to a control.
Figure 3:
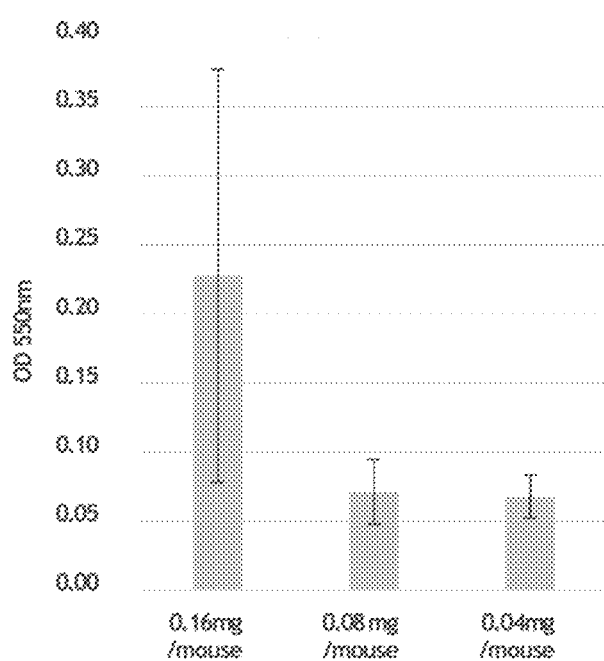
FIG. 3 is a graph of the level of zinc-charged insulin in mice who ingested the zinc-charged insulin in three low doses three hours post-ingestion.
Figure 4:
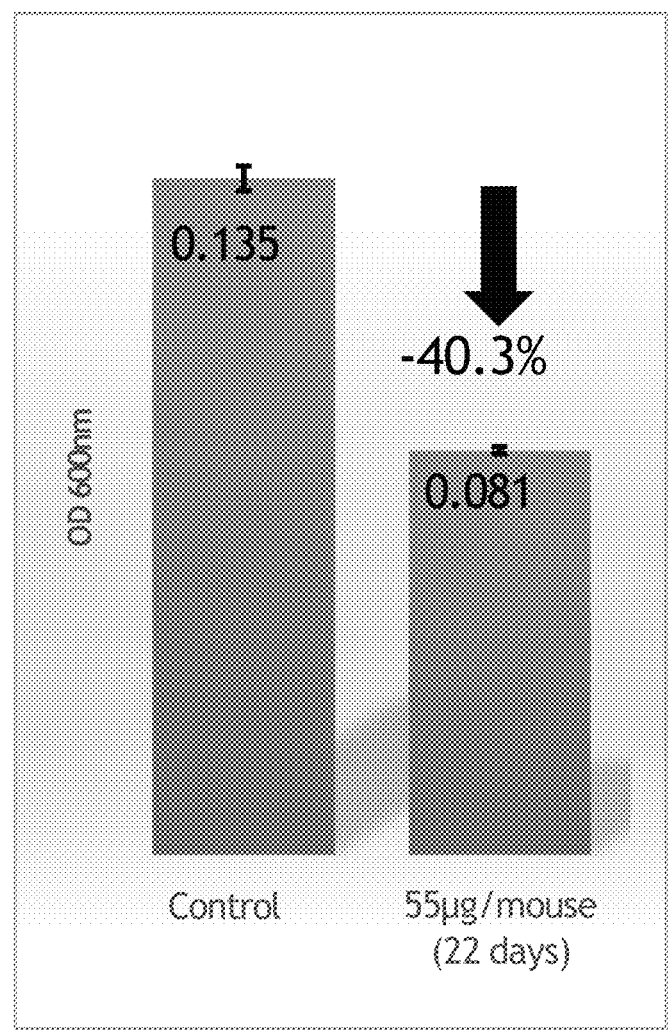
FIG. 4 is a graph of the levels of $HbA_{1c}$ in mice who ingested the zinc-charged insulin for 22 days before the $HbA_{1c}$ levels were read as compared to a control.

As shown in FIGS. 2-4, lower doses of the zinc-charged insulin was given to mice to determine the efficacy of orally administering low concentrations of the zinc-charged insulin. In these tests, the same control of uncharged insulin was administered to mice, as well as three new doses of zinc-charged insulin. Low Dose #1 contained the zinc-charged insulin dosed at 0.16 mg per mouse. Low Dose #2 contained the zinc-charged insulin dosed at 0.08 mg per mouse. Low Dose #3 contained the zinc-charged insulin dosed at 0.04 mg per mouse. Three hours after oral ingestion of the doses, the blood glucose levels of the mice were determined. Additionally, the amount of zinc-charged insulin present in the blood was also determined 3 hours post-ingestion.

As shown in FIG. 2, the blood glucose level of the mice given the control was just under 130 mg/dL. As with the doses shown in FIG. 1, the blood glucose levels of the mice given the zinc-charged insulin were lower as well. For the mice given Low Dose #1 (0.16 mg zinc-charged insulin per mouse), their blood glucose levels were measured near 97 mg/dL, or a 25% reduction from the control. For the mice given Low Dose #2 (0.08 mg zinc-charged insulin per mouse), their blood glucose levels were measured near 105 mg/dL, or a 19% reduction from the control. Lastly, for the mice given Low Dose #3 (0.04 mg zinc-charged insulin per mouse), their blood glucose levels were measured near 128 mg/dL, or an 2% reduction from the control.

Once the reduction in blood glucose was observed in the mice, the next determination was whether the zinc-charged insulin molecules were actually present in the blood stream. In order to make this determination, an Enzyme Linked Immunosorbent Assay ("ELISA") was performed to quantify the amount of zinc-charged insulin molecules in the blood stream. ELISA was also performed on uncharged insulin as a control, as with the testing shown in FIG. 2. Here, the ELISA assay involved having proteins from the blood sample absorbed onto a plate in the assay. As zinc-charged bovine insulin was utilized in this study, a first antibody against bovine insulin was incubated at the top of the well. After extensive washing, a second matching antibody which was tagged with an enzyme was incubated for binding to the first antibody, then exposed to a substrate of the enzyme. If there was binding in the last reaction, a detectable signal can be observed. Generally, the detectable signal is based on a color change of the substance, which can be observed at different wavelengths.

Here, to determine the levels of zinc-charged insulin in the blood sample, the optical density (OD) of the blood sample was taken at a wavelength of 550 nm after the ELISA assay was performed. If the zinc-charged insulin was effectively absorbed into the blood stream then a color change in the ELISA assay would be expected, such that the presence of zinc-charged insulin may be measured using the OD of the blood sample. However, if no color is observed, this result would indicate a lack of binding in the last reaction in the ELISA assay, indicating a lack of absorption of the zinc-charged insulin into the blood stream.

As shown in FIG. 3, for the mice given Low Dose #1 (0.16 mg zinc-charged insulin per mouse), the OD was measured at approximately 0.23, indicating the presence of the zinc-charged insulin in the blood. For the mice given Low Dose #2 (0.08 mg zinc-charged insulin per mouse), the OD was measured at approximately 0.07, also indicating the presence of the zinc-charged insulin in the blood. For the mice given Low Dose #3 (0.04 mg zinc-charged insulin per mouse), the OD was measured at approximately 0.06, also indicating the presence of the zinc-charged insulin in the blood. For the control, no color was observed in the sample, indicating that the control of uncharged insulin was not absorbed by the blood stream. As such, this data confirms that the zinc-charged insulin survived oral administration and was absorbed into the blood stream.

FIG. 4 depicts the levels the $HbA_{1c}$ in mice after the lowest effective dose of zinc-charged insulin for mice was administered for a period of 22 days. For this test, the mice were orally administered the lowest effective dose of the zinc-charged insulin at 55 µg per mouse. After 22 days of feeding the mice with 55 µg zinc-charged insulin, the $HbA_{1c}$ levels were read. It was discovered that after 22 days of administering the lowest effective dose, the amount of $HbA_{1c}$ in the blood had been reduced by 40.3% when compared to the control. Thus, administering this lowest effective dose of the zinc-charged insulin for mice still had a positive effect on the levels of blood glucose, further demonstrating the efficacy of the zinc-charged insulin when orally administered.

Figure 5:
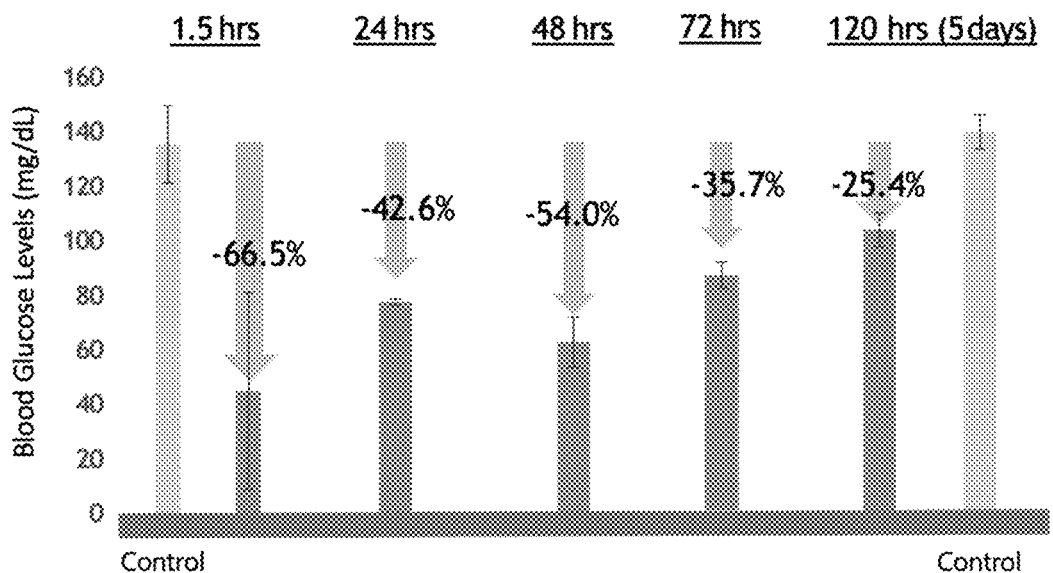
FIG. 5 is a graph of the blood glucose levels of mice who ingested the zinc-charged insulin over a five-day period, as compared to a control.
Figure 6:
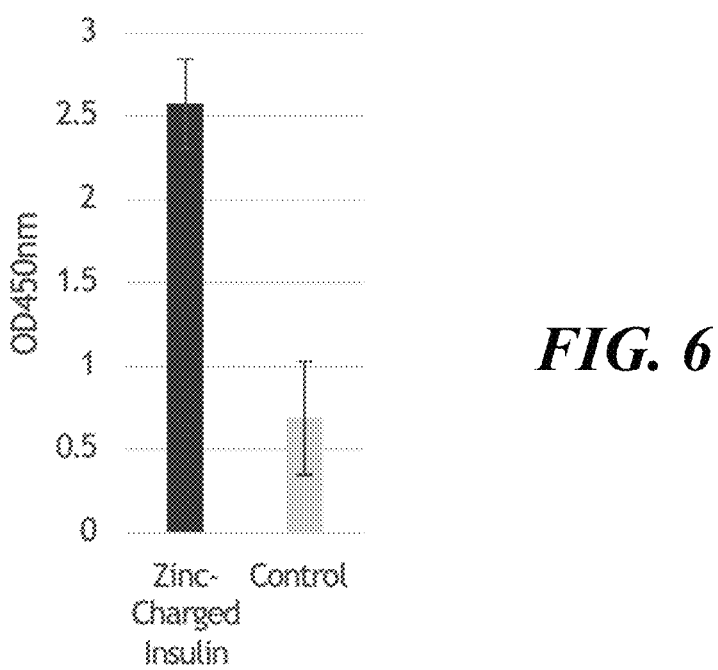
FIG. 6 is a graph of the erythrocyte insulin receptor activity in mice who ingested the zinc-charged insulin five days prior, as compared to a control.

FIGS. 5-6 depict the long-lasting effectiveness of the zinc-charged insulin in mice. For this test, 0.25 mg of zinc-charged insulin containing 10 mg of glucose was orally administered to mice who had been fasting for 12 hours. For the control, 2.5 mg of uncharged insulin containing 10 mg of glucose was orally administered to mice who had also been fasting for 12 hours. Blood glucose was then measured at 1.5 hours, 24 hours, 48 hours, 72 hours, and 120 hours.

As shown in FIG. 5, the mice who were given the control had close to 140 mg/dL of blood glucose both at the 1.5 hour mark and the 120 hour mark. The results of the mice given the control further highlight the inefficacy of orally administering uncharged insulin. The mice who were given the 0.25 mg of zinc-charged insulin saw significant reductions in blood glucose over the 120-hour period. At the 1.5-hour mark, the mice having the zinc-charged insulin saw a 66.5% reduction in blood glucose compared to the control. At the 24-hour mark, their blood glucose levels showed a 42.6% reduction in blood glucose when compared to the control. At the 48-hour mark, their blood glucose levels showed a 54.0% reduction in blood glucose, the 72-hour mark showed a 35.7% reduction in blood glucose. The 120-hour mark still showed a 25.4% reduction in blood glucose when compared with the control. The zinc-charged insulin thus remains effective even after 120 hours.

The presence of zinc-charged insulin in the mice blood is further highlighted by the activation of the insulin receptor in the mice erythrocytes, as shown in FIG. 6. In this experiment, mice were fed with zinc-charged insulin, followed by the withdrawal of erythrocytes from the mice. The insulin receptor on the erythrocytes surface was isolated, and the phosphorylation state, which reflects the activity of the insulin receptor, was determined (manifestation by OD450). Since the insulin receptor is only activated by insulin, the higher activity of the insulin receptor, which results in higher phosphorylation of the insulin receptor, provides evidence that exogenous insulin was added to the blood stream.

Further, as shown in FIGS. 16 and 17, the effective application of this technology to other commercially available subcutaneously injected insulin products was shown through mice testing. As discussed above, FIGS. 16 and 17 show a reduction in blood glucose in mice who were orally administered 0.8 mg of zinc-charged insulin Lispro or zinc-charged insulin Glargine. These results further suggest that the method disclosed herein is capable of converting not only general uncharged insulin into insulin that is orally available, but also commercially available subcutaneously injected insulin products into insulin that can be orally administered.

(2) Zinc-Charged Insulin Administered Orally: Effects in Humans

Once the oral administration of the zinc-charged insulin was shown effective on mice, the efficacy on human subjects was analyzed and confirmed. FIGS. 7-16 provide the graphs depicting the results of the testing on the human subjects.

FIGS. 7-13h depict the effect of the zinc-charged insulin administered orally to human subjects when compared to the control. Specifically, FIGS. 7-13h show the blood glucose levels of human subjects after orally administering glucose in predetermined intervals after administration of the zinc-charged insulin. For each of the tests depicted in FIGS. 7-13h, the control subject was only provided the glucose dose without having the zinc-charged insulin dose administered prior.

For these tests, the human subject fasted overnight, such that the human subjects were in a state of fasting for the blood glucose tests. For each non-control human subject, the subject was orally administered 15 mg of zinc-charged insulin. All of the human subjects then waited for a predetermined amount of time, then had 12 g of glucose administered. The subject's blood glucose levels where then tracked for up to 210 minutes after the administration of the glucose to determine whether there was a reduction in the amount of blood glucose compared to the control. The blood glucose levels were determined by the measurement of AUC (the "area under curve").

Figure 7:
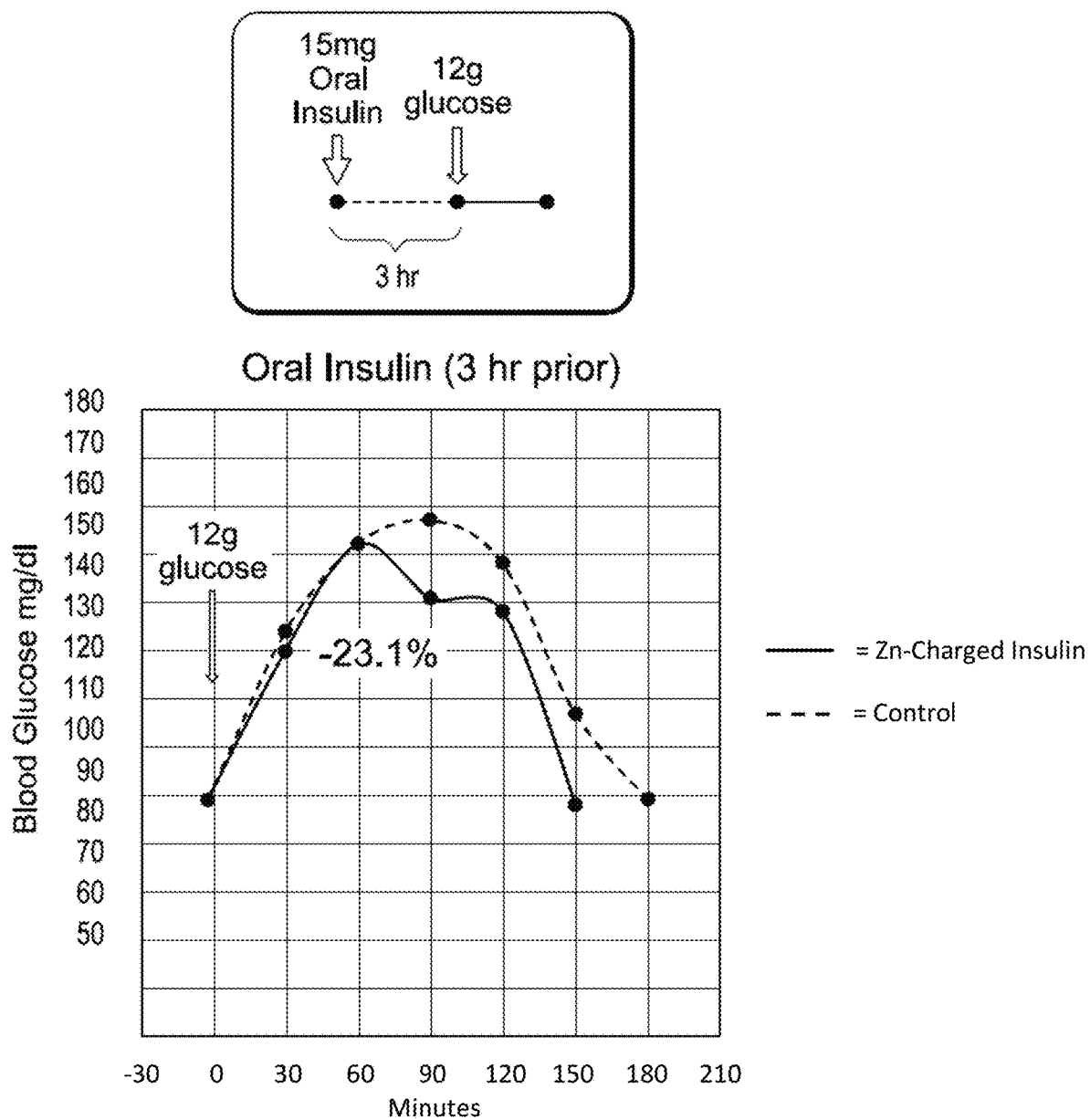
FIG. 7 is a graph of the efficacy of the zinc-charged insulin as orally administered to a human subject 3 hours prior to the administration of the glucose, as compared to a control.

FIG. 7 depicts this test when the zinc-charged insulin was administered 3 hours prior to the administration of the glucose, herein the "3-hour interval". As shown in this figure, the amount of blood glucose in subject who took the zinc-charged insulin was reduced by 23.1% overall, with significant reductions in the blood glucose after the first 60 minutes. Ultimately, the blood glucose levels in the subject who was orally given the zinc-charged insulin was less than the blood glucose levels in the subject who was orally given the control. Thus, the oral administration of the zinc-charged insulin was effective in reducing the levels of blood glucose during the 3-hour interval.

Figure 8:
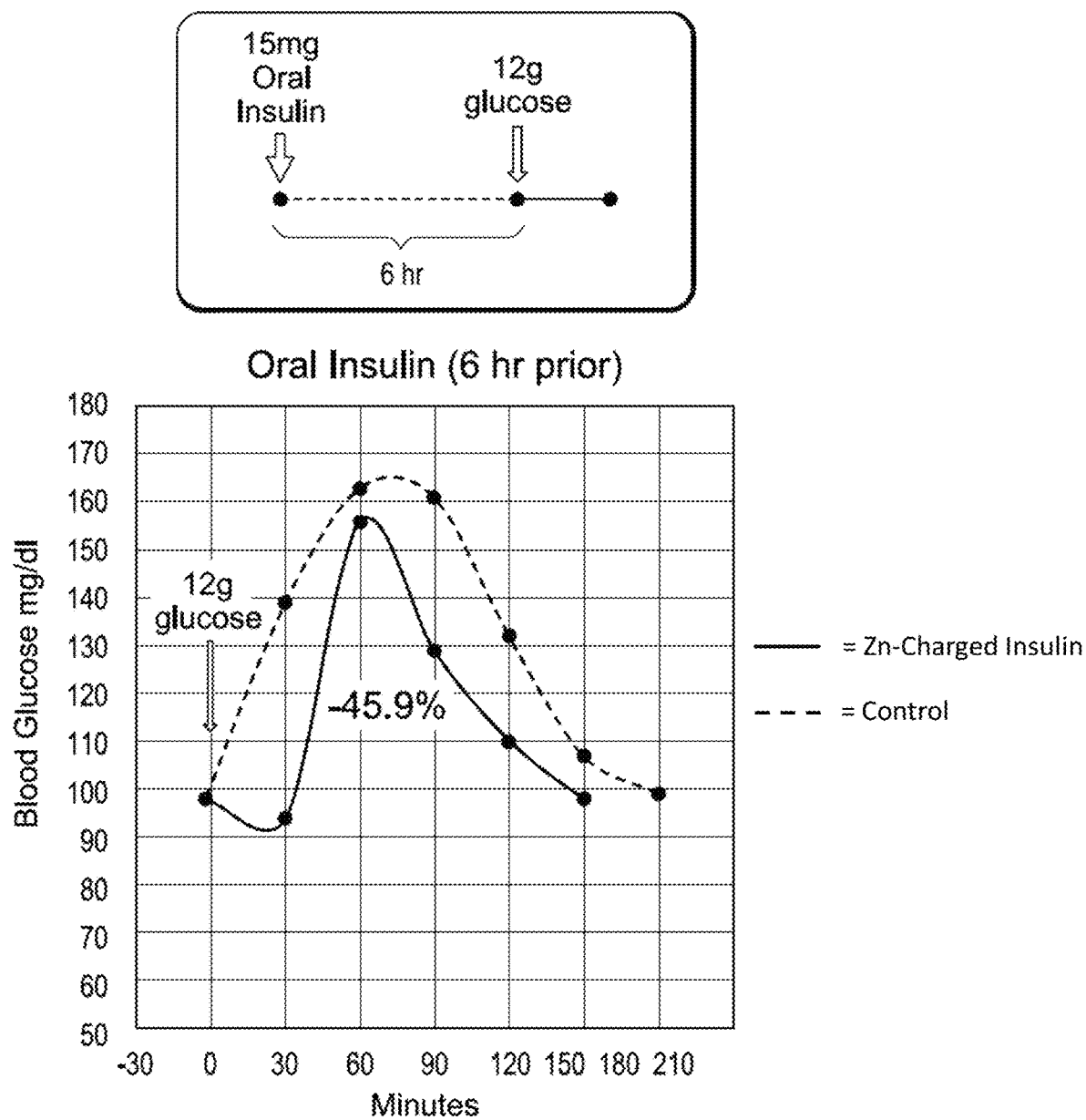
FIG. 8 is a graph of the efficacy of the zinc-charged insulin as orally administered to a human subject 6 hours prior to the administration of the glucose, as compared to a control.

FIG. 8 depicts this test when the zinc-charged insulin was administered 6 hours prior to the administration of the glucose, herein the "6-hour interval". As shown in this figure, the amount of blood glucose in subject who took the zinc-charged insulin was reduced by 45.9% overall, with significant reductions in the blood glucose throughout the 210 minutes. The blood glucose levels in the subject who was orally given the zinc-charged insulin was less than the blood glucose levels in the subject who was orally given the control throughout the entire time period. Thus, the oral administration of the zinc-charged insulin was significantly effective in reducing the levels of blood glucose during the 6-hour interval.

Figure 9:
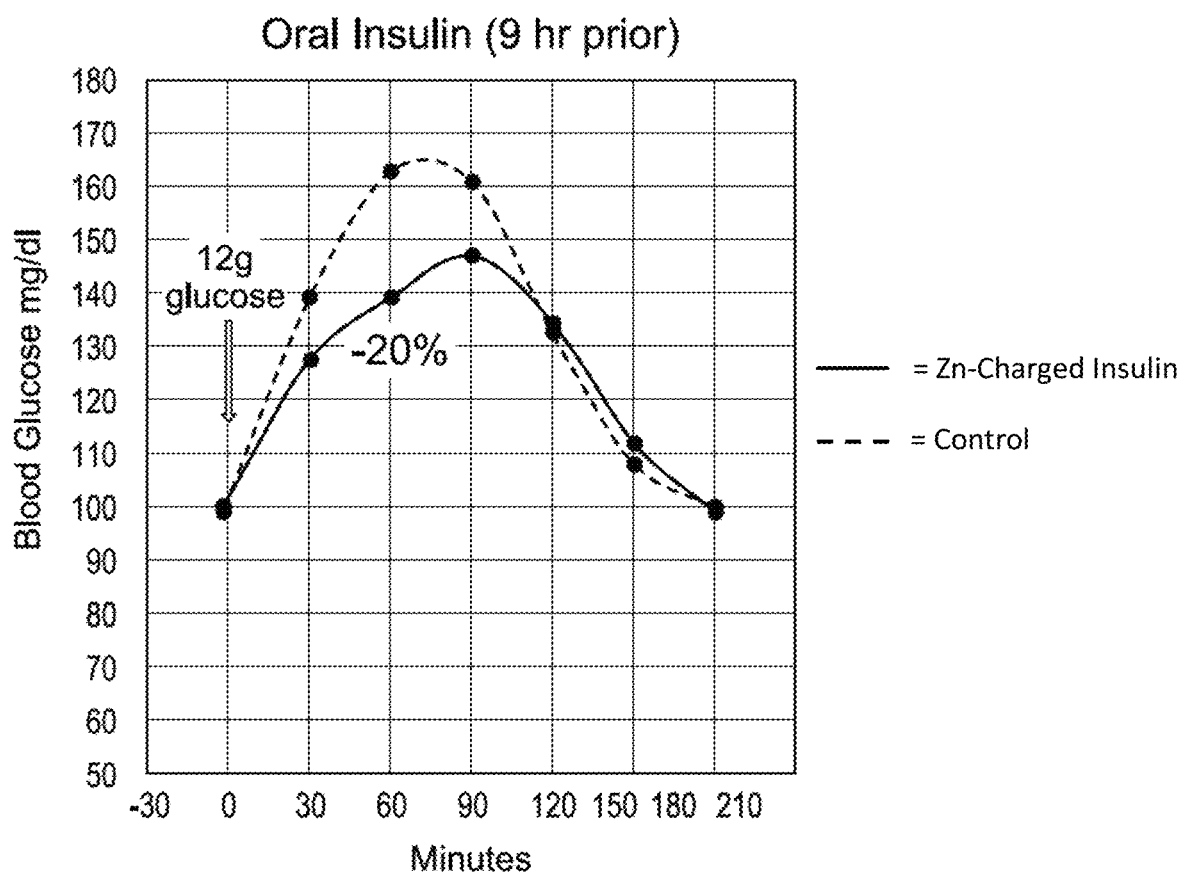
FIG. 9 is a graph of the efficacy of the zinc-charged insulin as orally administered to a human subject 9 hours prior to the administration of the glucose, as compared to a control.

FIG. 9 depicts this test when the zinc-charged insulin was administered 9 hours prior to the administration of the glucose, herein the "9-hour interval". As shown in this figure, the amount of blood glucose in subject who took the zinc-charged insulin was reduced by 20% overall, with significant reductions in the blood glucose during the first 90 minutes after administration of the glucose. The blood glucose levels in the subject who was orally given the zinc-charged insulin was less than the blood glucose levels in the subject who was orally given the control until the 120-minute mark. Thus, the oral administration of the zinc-charged insulin was effective in reducing the levels of blood glucose during the 9-hour interval as well, further confirming that the zinc-charged insulin remained effective after oral administration.

Figure 10:
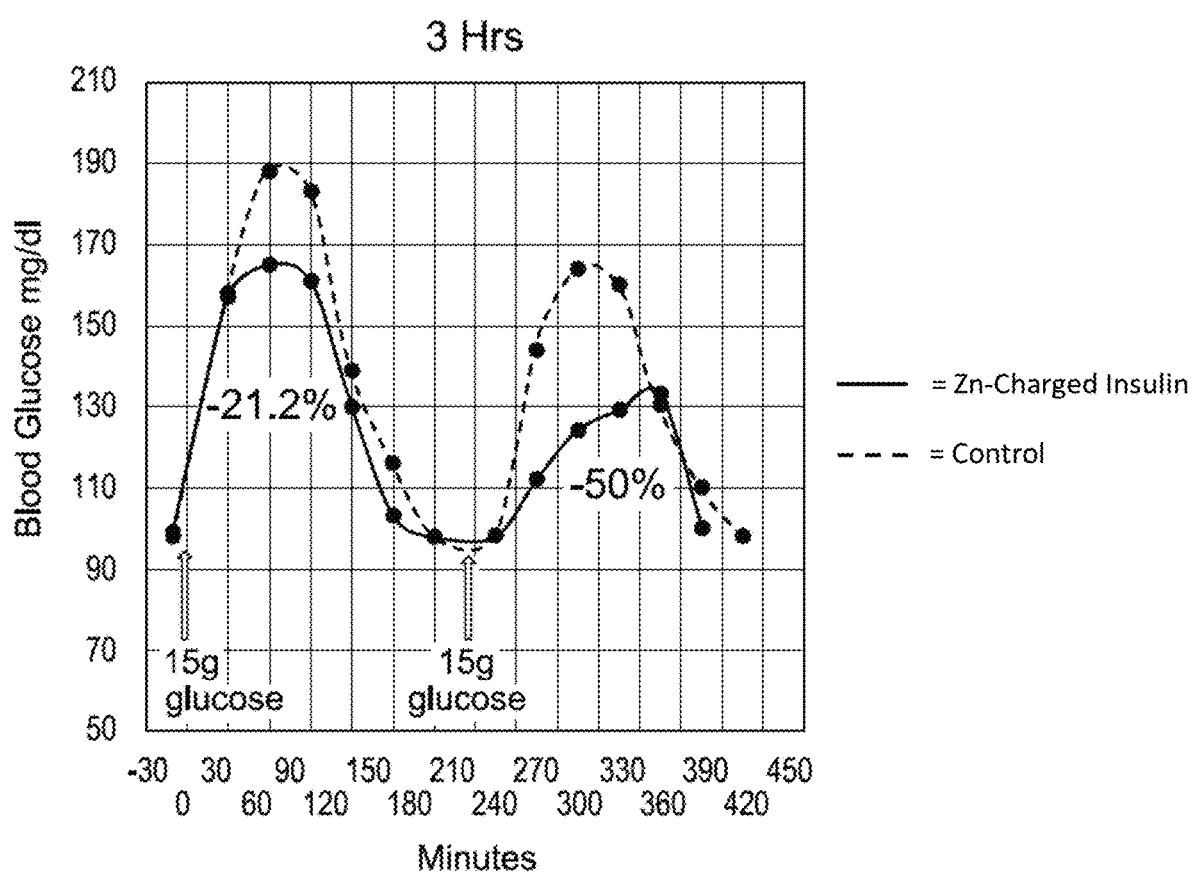
FIG. 10 is a graph of the blood glucose levels of human subjects after administering two separate doses of glucose three hours after oral administration of the zinc-charged insulin, as compared to a control.
Figure 11:
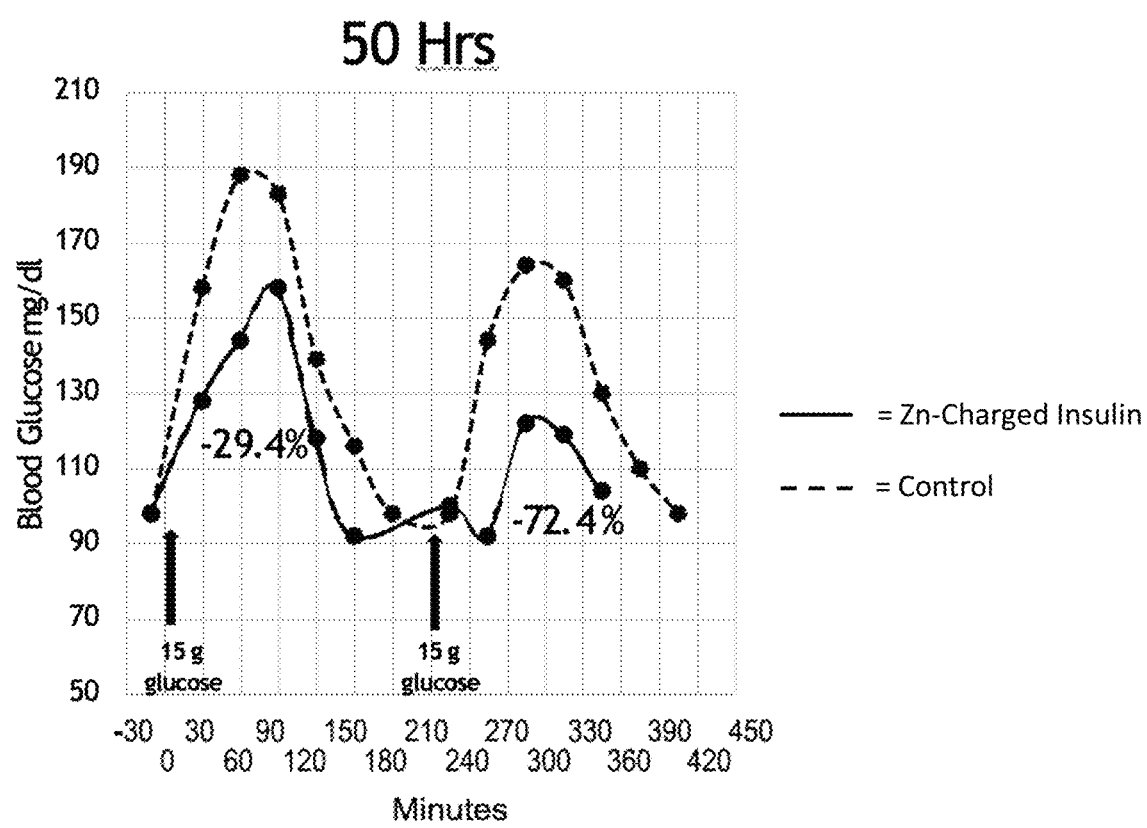
FIG. 11 is a graph of the blood glucose levels of human subjects after administering two separate doses of glucose fifty hours after oral administration of the zinc-charged insulin, as compared to a control.
Figure 12:
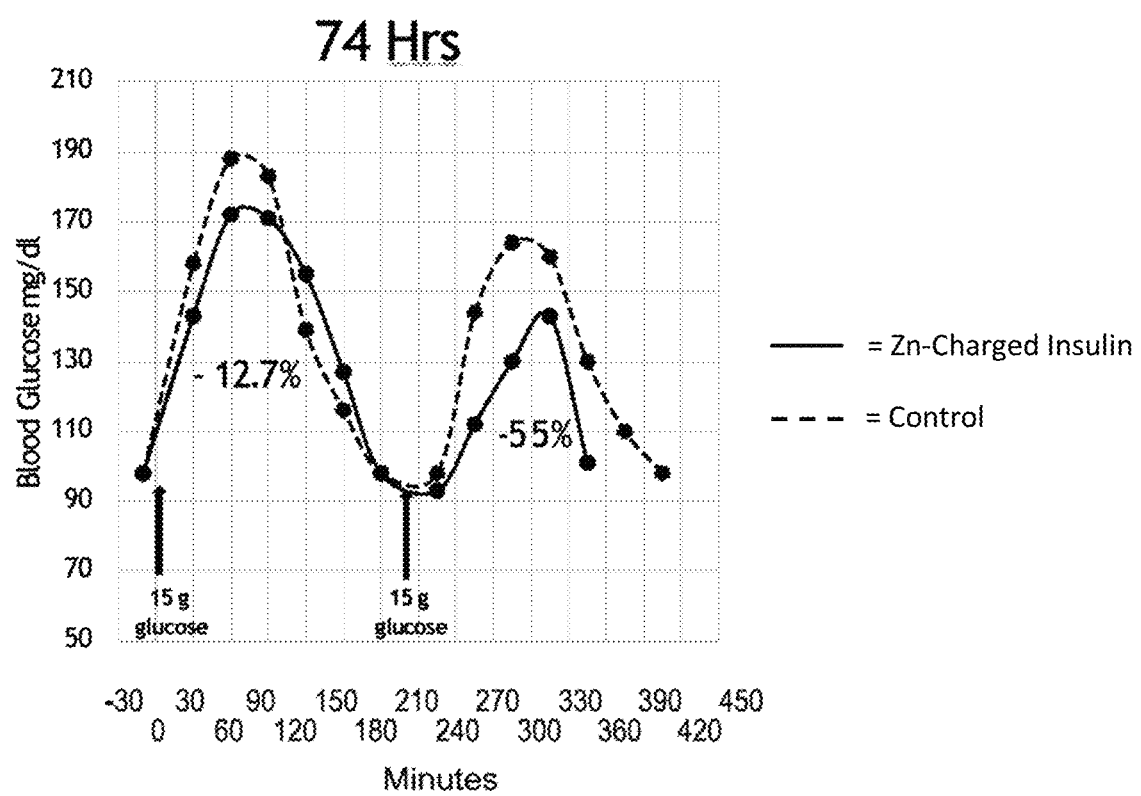
FIG. 12 is a graph of the blood glucose levels of human subjects after administering two separate doses of glucose seventy-four hours after oral administration of the zinc-charged insulin, as compared to a control.
Figure 13A:
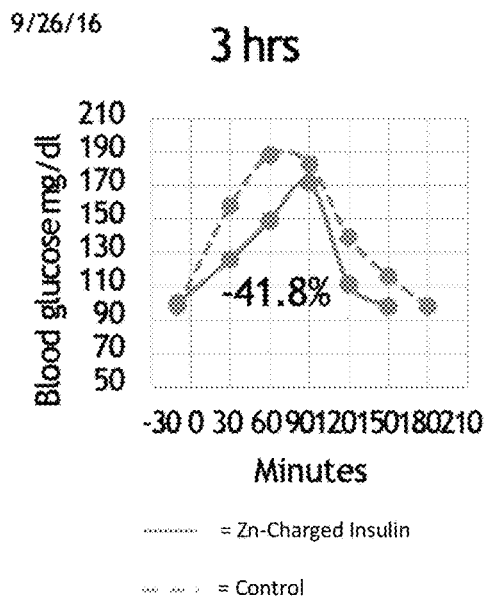
FIGS. 13a-13h are a sequence of graphs depicting the blood glucose levels of a human subject taken at various times over a 14-day period.
Figure 13B:
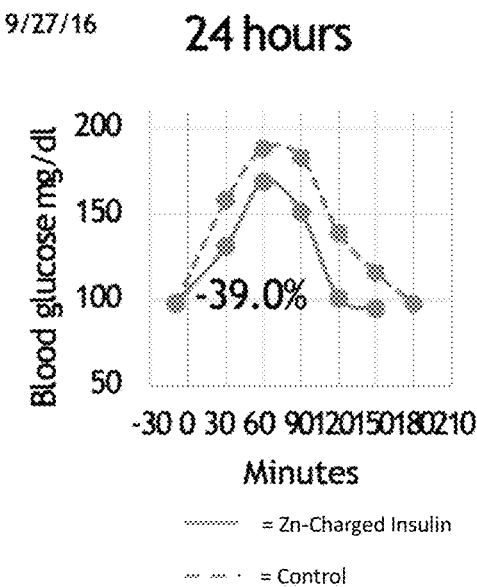
Figure 13C:
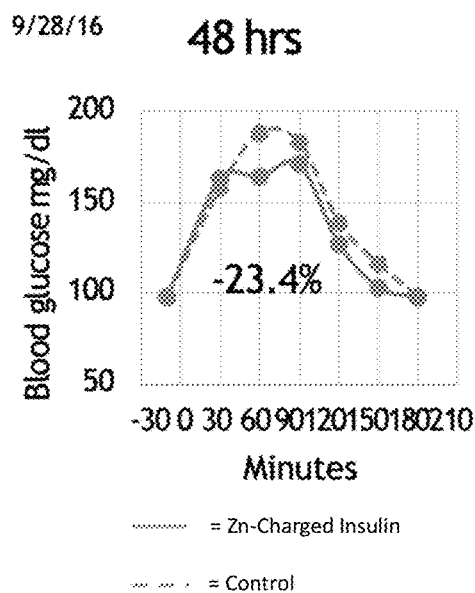
Figure 13D:
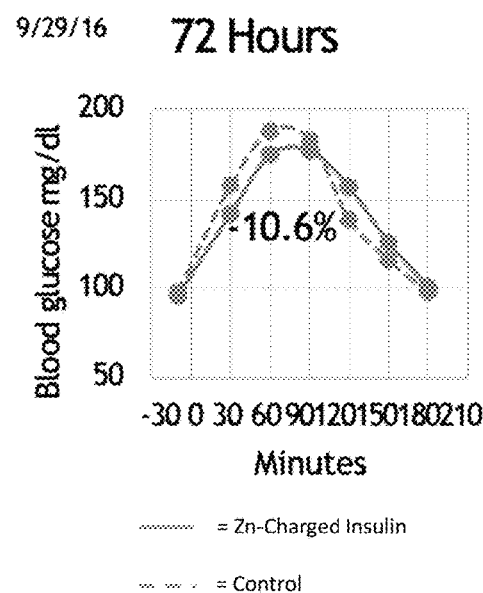
Figure 13E:
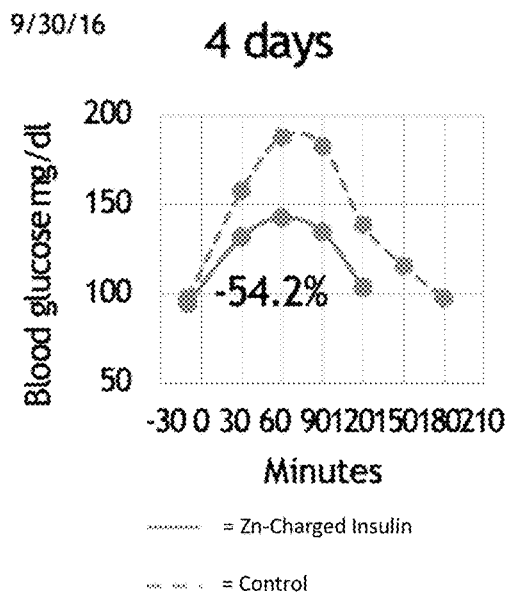
Figure 13F:
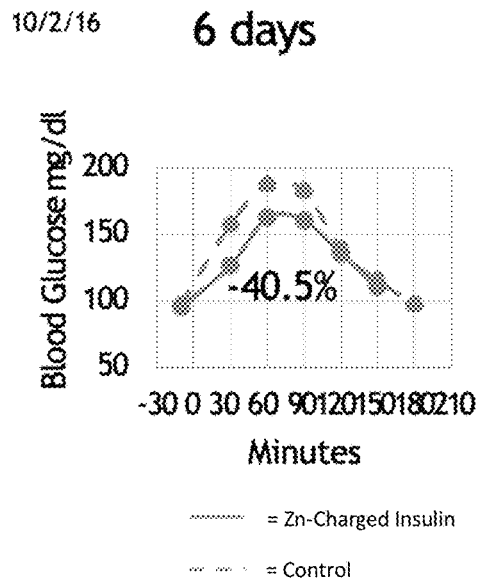
Figure 13G:
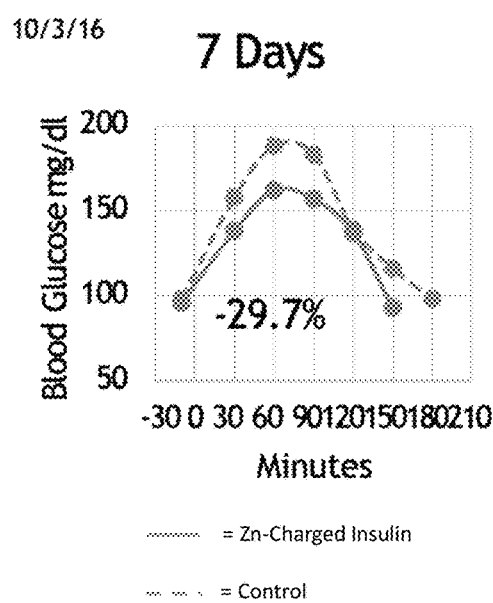
Figure 13H:
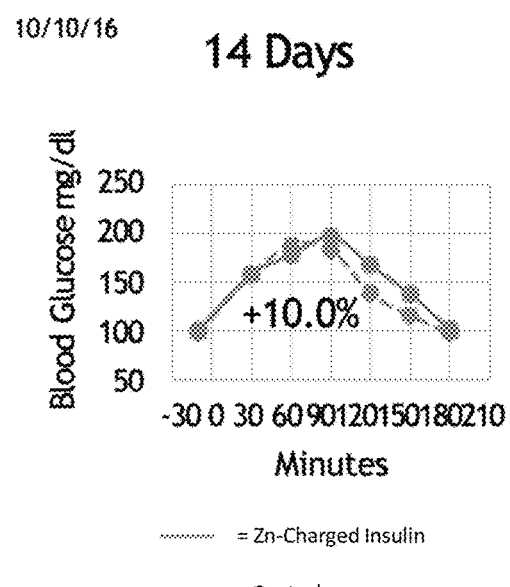

FIGS. 10-12 depict the effect of orally administering 15 mg of the zinc-charged insulin a to human subject. Specifically, FIGS. 10-12 show the blood glucose levels of human subjects after administering glucose at two different times during a 420-minute period for each predetermined time interval after oral administration of 15 mg of the zinc-charged insulin. The three predetermined time intervals were 3 hours after ingestion, 50 hours after ingestion, and 74 hours after ingestion of the zinc-charged insulin. As with the prior human testing, the control for these tests were based on oral administration of glucose only.

In the graphs depicted in FIGS. 10-12, the area under the curves reflect the total blood glucose in each subject. Thus, a reduction in the area under the curve reflects a reduction in the total blood glucose in the subject.

As shown in FIG. 10, a human subject was orally administered 15 mg of zinc-charged insulin, then given a first dose of 15 g of glucose 3 hours after ingestion of the zinc-charged insulin, then given a second dose of 15 g of glucose approximately 240 minutes after the first dose. The control showed a curve with a large amplitude, having two large peaks around the 60-minute mark and the 300-minute mark, reflecting a large area under the curves for the control. Yet, the human subject given the zinc-charged insulin showed significant reduction in the area under the curve, having the area under the first peak reduced by 21.2% and the area under the second peak reduced by 50.0%. Additionally, the overall curves are leveled out and the total area under the curve is reduced, further highlighting the efficacy of the zinc-charged insulin when orally administered.

As shown in FIG. 11, a human subject was orally administered 15 mg of zinc-charged insulin, then given a first dose of 15 g of glucose 50 hours after ingestion of the zinc-charged insulin, then given a second dose of 15 g of glucose approximately 240 minutes after the first dose. As with the prior test, the control showed a curve with a large amplitude, having two large peaks around the 60-minute mark and the 300-minute mark. Yet, the human subject given the zinc-charged insulin showed an even larger reduction in the area under the curve, having the first peak reduced by 29.4% and the second peak reduced by 72.4%. Additionally, the overall curves are further leveled out and the total area under the curve is reduced, highlighting the efficacy of the zinc-charged insulin when orally administered.

As shown in FIG. 12, a human subject was orally administered 15 mg of zinc-charged insulin, then given a first dose of 15 g of glucose 74 hours after ingestion of the zinc-charged insulin, then given a second dose of 15 g of glucose approximately 240 minutes after the first dose. As with the prior tests, the control showed a curve with a large amplitude, having two peaks around the 60-minute mark and the 300-minute mark. Yet, the human subject given the zinc-charged insulin still showed a reduction in the area under the curve, having the first peak reduced by 12.7% and the second peak reduced by 55%. While this reduction was not as significant as the two prior time intervals, the peaks were still reduced and stabilized and the total area under the curve was reduced, also highlighting the efficacy of the zinc-charged insulin when orally administered, even after 74 hours.

FIGS. 13*a*-13*h* (referred to as FIG. 13 together) depicts a sequence of graphs showing the blood glucose levels of a human subject taken at various times over a 14-day period. To establish a control, the human subject was first given a control of 15 g of glucose, and their blood glucose levels were determined to set the baseline. The next day, the same human subject was orally given 15 g of glucose containing 15 mg of zinc-charged insulin. Utilizing a single human subject for comparing the control and zinc-charged insulin doses is important to establish an accurate comparison, as biological differences between humans can be significant.

The subject was then given glucose at various time periods to determine the efficacy of the zinc-charged insulin over time. The first graph (FIG. 13*a*) depicts the glucose tolerance 3 hours after oral administration of the control and zinc-charged insulin. As with the first graph, the second graph (FIG. 13*b*) depicts the glucose tolerance 24 hours after oral administration of the control and zinc-charged insulin, the third graph (FIG. 13*c*) depicts the glucose tolerance 48 hours after oral administration of the control and zinc-charged insulin, the fourth graph (FIG. 13*d*) depicts the glucose tolerance 72 hours after oral administration of the control and zinc-charged insulin, the fifth graph (FIG. 13*e*) depicts the glucose tolerance 4 days after oral administration of the control and zinc-charged insulin, the sixth graph (FIG. 13*f*) depicts the glucose tolerance 6 days after oral administration of the control and zinc-charged insulin, the seventh graph (FIG. 13*g*) depicts the glucose tolerance 7 days after oral administration of the control and zinc-charged insulin, and the eighth graph (FIG. 13h) depicts the glucose tolerance 14 days after oral administration of the control and zinc-charged insulin.

This sequence of graphs depicted in FIG. 13 displays the effectiveness of the zinc-charged insulin when orally administered in direct comparison to uncharged insulin orally administered to the same subject. First, 3 hours after oral ingestion of 15 mg zinc-charged insulin, the human subject saw a 41.8% decrease in blood glucose levels when compared to the control. This trend continued over time, further highlighting the continued effectiveness of the zinc-charged insulin orally administered. 24 hours after oral ingestion of the 15 mg zinc-charged insulin, the human subject experienced a 39.0% reduction in blood glucose. 48 hours after oral ingestion of the 15 mg zinc-charged insulin, the human subject experienced a 23.4% reduction in blood glucose. This trend continued up to a week post-ingestion, with the testing showing a 54.2% reduction in blood glucose levels 4 days post-ingestion, a 40.5% reduction in blood glucose levels 6 days post-ingestion, and a 29.7% reduction in blood glucose levels 7 days post-ingestion. Not until 14 days post-ingestion did the testing show no further reduction in blood glucose levels. Thus, the zinc-charged insulin was capable of reducing and stabilizing the human subject's blood glucose levels for nearly two weeks post-ingestion, further highlighting the efficacy of the zinc-charged insulin orally administered to a subject.

Further, this testing highlights the long-lasting nature of the zinc-charged insulin in stabilizing blood glucose levels. Thus, the zinc-charged insulin may be effectively administered at any dose frequency up to one dose every two weeks. Preferably, the zinc-charged insulin is administered once per week to maintain the levels of zinc-charged insulin in the body, thereby keeping a patient's blood glucose levels stable for at least a week at a time.

Figure 14:
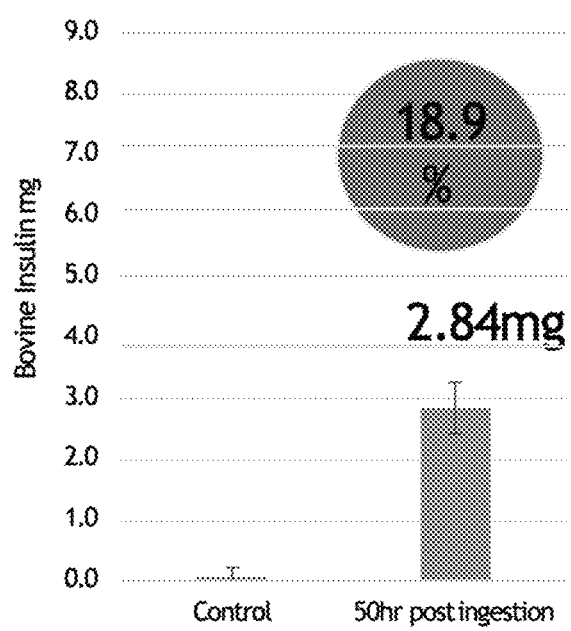
FIG. 14 is a graph of the quantity of zinc-charged insulin in the human subject's blood stream 50 hours post-ingestion, as compared to a control.
Figure 15:
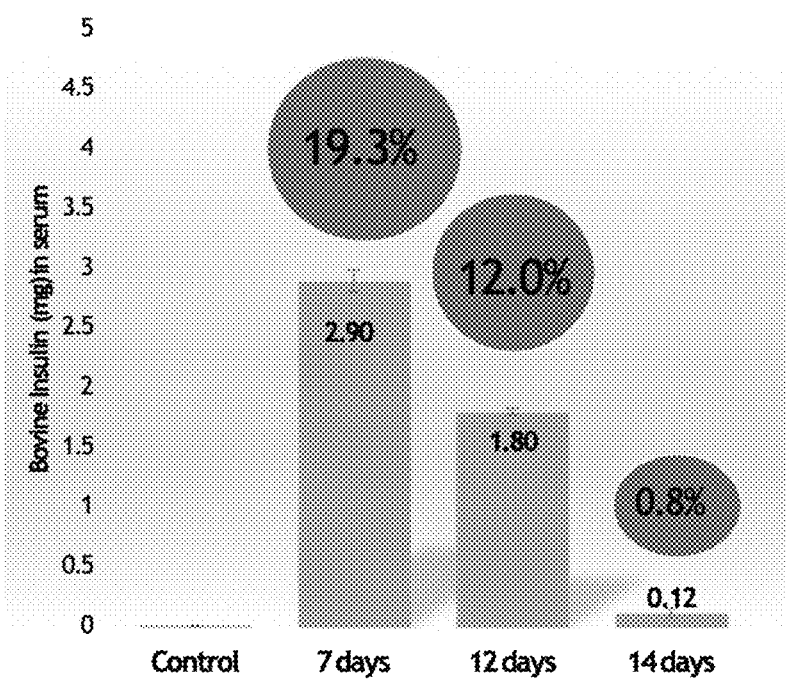
FIG. 15 is a graph of the quantity of zinc-charged insulin remaining in the blood of a human subject 7 days, 12 days, and 14 days post-ingestion, as compared to a control.

FIGS. 14-15 show the levels over time of zinc-charged insulin detected in the subject's blood after oral ingestion, further confirming the ability for the zinc-charged insulin to survive the stomach acid and digestion enzymes and be absorbed by the GI tract. FIG. 14 depicts the quantity of zinc-charged insulin in the human subject's blood stream 50 hours post-ingestion. For these tests, 15 mg of zinc-charged insulin was given to the subject, and the subject's blood was then analyzed by ELISA assay as described above, then analyzed at different periods of time post-ingestion to determine how much of the zinc-charged insulin remained in the blood. For the control, uncharged insulin was orally administered to a human subject instead of zinc-charged insulin.

As shown, 50 hours post-ingestion, 2.84 mg of the zinc-charged insulin was still present in the human subject's blood, or 18.9% of the original 15 mg zinc-charged insulin orally administered. The control showed 0 mg of the uncharged insulin in the blood. This comparison further shows the inefficacy of uncharged insulin orally administered, while confirming the efficacy of the orally administered zinc-charged insulin in being absorbed into the blood stream.

FIG. 15 depicts the quantity of zinc-charged insulin remaining in the blood of a subject 7 days, 12 days, and 14 days post-ingestion. As shown, 7 days after oral administration of the 15 mg zinc-charged insulin, 2.90 mg of the zinc-charged insulin remained in the human blood, or 19.3%. After 12 days, 1.80 mg of the zinc-charged insulin remained in the blood, or 12.0%. After 14 days, 0.12 mg of the zinc-charged insulin remained, or 0.8%. As with the prior tests, the control of uncharged insulin administered orally failed to detect any insulin in the blood stream after 7 days, 12 days, or 14 days.

Importantly, the detection of zinc-charged insulin in the blood stream up to 14 days post-ingestion aligns with the reductions in blood glucose over time shown in FIG. 13. The 2.84 mg of zinc-charged insulin detected in the blood stream at the 50-hour mark aligns with the 23.4% reduction in blood glucose 48 hours post-ingestion from FIG. 13c, while the 2.90 mg of zinc-charged insulin detected at the 7-day mark aligns with the 29.7% reduction in blood glucose 7-days post-ingestion from FIG. 13g. Further, the 0.12 mg of zinc-charged insulin detected in the blood stream 14 days post ingestion matches the lack of reduction in blood sugar shown 14-days post ingestion in FIG. 13h. This testing further supports the long-lasting effects of the zinc-charged insulin in the body, as the zinc-charged insulin is still present in significant levels 7-days post-ingestion.

Therefore, based upon the testing performed on mice and humans, the zinc-charged insulin may be orally administered without losing all effectiveness. Utilizing the above discussed composition and method of preparation, the zinc-charged insulin molecule with the zinc ion cloud may survive oral ingestion and be significantly absorbed into the blood stream through the GI tract, unlike uncharged insulin molecules.

What is claimed is:
1. A composition comprising:
    a zinc-charged insulin composition having a plurality of zinc ions bound to the surface of an insulin molecule in a ratio of said insulin molecule to said zinc ions of approximately 1:137 wherein said zinc-charged insulin composition is intended for oral administration.
2. The composition of claim 1, wherein said insulin zinc-charged insulin composition is administered as a capsule.
3. The composition of claim 1, wherein said zinc-charged insulin composition is administered as a pressed tablet.
4. The composition of claim 1, wherein said zinc-charged insulin composition is administered as a liquid.

* * * * *